United States Patent [19]

Nashef

[11] Patent Number: 4,729,139

[45] Date of Patent: Mar. 8, 1988

[54] SELECTIVE INCORPORATION OF A POLYMER INTO IMPLANTABLE BIOLOGICAL TISSUE TO INHIBIT CALCIFICATION

[75] Inventor: Aws S. Nashef, Costa Mesa, Calif.

[73] Assignee: Baxter Travenol, Deerfield, Ill.

[21] Appl. No.: 795,124

[22] Filed: Nov. 5, 1985

[51] Int. Cl.$^4$ .................. A61L 17/00; A63B 51/02; D01Q 3/00; D01F 5/00

[52] U.S. Cl. .................. 8/94.11; 8/94.21; 623/2

[58] Field of Search .............. 8/94.11, 94.21, 1, 1.4, 8/1.5; 623/2

[56] References Cited

U.S. PATENT DOCUMENTS

| | | | |
|---|---|---|---|
| 4,066,583 | 1/1978 | Spaulding | 260/17.4 |
| 4,120,649 | 10/1978 | Schechter | 8/94.1 R |
| 4,182,750 | 1/1980 | Sullivan et al. | 424/1 |
| 4,314,800 | 2/1982 | Monsheimer et al. | 8/94.19 |
| 4,323,358 | 4/1982 | Lentz et al. | 8/94.11 |
| 4,350,806 | 9/1982 | Wagener | 528/289 |
| 4,369,036 | 1/1983 | Saito et al. | 8/115.5 |
| 4,377,010 | 3/1983 | Fydelor et al. | 8/94.11 |
| 4,378,224 | 3/1983 | Nimni et al. | 8/94.11 |
| 4,383,832 | 5/1983 | Fraefel et al. | 8/94.11 |
| 4,402,697 | 9/1983 | Pollock et al. | 8/94.11 |
| 4,481,009 | 11/1984 | Nashef | 8/94.11 |
| 4,511,478 | 4/1985 | Nowinski et al. | 525/54.1 |

OTHER PUBLICATIONS

Brauer, G. M. and D. J. Termini, *J. of Applied Polymer Sci.*, vol. 17, pp. 2557–2568 (1973).

Ratner, B. D. and A. S. Hoffman, "Synthetic Hydrogels for Biomedical Applications", in *Hydrogels for Med. and Related Applications*, J. Andrade, Ed., ACS Symposium Series, 31, pp. 1–36 (1976).

Lloyd, D. and C. Burns, *J. of Polymer Science: Polymer Chem. Edition*, vol. 17, pp. 3473–3483 (1979).

*Primary Examiner*—Paul Lieberman
*Assistant Examiner*—John F. McNally
*Attorney, Agent, or Firm*—Bernard, Rothwell & Brown

[57] ABSTRACT

A process for selectively incorporating biocompatible polymers in the interstices of implantable biological tissue while leaving the outer surface of the tissue substantially free of bonded polymer. The process involves covalently binding a monomer to the tissue, contacting the tissue with a free-radical initiator, then contacting the tissue with a solution containing a second monomer and a free-radical scavenger, thereby promoting selective polymerization of the second monomer with the portion of covalently-bound first monomer which is located in the interstices of the tissue.

29 Claims, No Drawings

SELECTIVE INCORPORATION OF A POLYMER INTO IMPLANTABLE BIOLOGICAL TISSUE TO INHIBIT CALCIFICATION

BACKGROUND OF THE INVENTION

With the introduction of glutaraldehyde preservation of biological tissue, and in particular porcine bioprosthetic heart valves, it has been possible to: (a) overcome the poor performance of early formaldehyde-preserved implanted tissue valves; (b) discontinue the use of homograft valves; and (c) avoid the undesirable use of anticoagulants required to prevent thromboembolism associated with the use of non-bioprosthetic (mechanical) heart valves especially in children. Not unlike similarly important discoveries, however, it appears that the glutaraldehyde-preserved bioprosthesis has created its own dilemma.

Although the relatively biologically inert glutaraldehyde-preserved valves of Carpentier and others have demonstrated excellent long-term durability in most instances, serious drawbacks such as tissue-fatigue and a propensity toward calcification have plagued its continued use. Moreover, it was initially contemplated that children and adolescents would be among those deriving the greatest benefit from the glutaraldehyde-preserved bioprosthetic heart valves since the anticoagulants required with mechanical prosthesis could be eliminated. Results from an increasing number of recent clinical studies, however, indicate that severe calcification of these tissues with relatively short-term failure is prevalent among children and adolescents. Thus, despite their long-term durability and overall reduced incidence of complications, these glutaraldehyde-preserved valves have been deemed by some to be unsuitable for use in children.

Calcification of tissue remains a mystery for the most part; however, it has previously been shown that various factors including calcium metabolism diseases, age, diet, degeneration of tissue components such as collagen, and turbulance are all involved to a certain extent. Recently, the occurrence of a specific calcium-binding amino acid, laid down after implantation of glutaraldehyde-preserved porcine xenografts, has been demonstrated; and it has been postulated to play a role in calcification. While calcification has been accompanied by degradative changes in the glutaraldehyde-treated collagen fibers of the implanted tissue, it remains unclear whether the dystrophic calcification is a cause or the result of tissue degradation. Nevertheless, there has been a continued effort to elucidate the source of the calcification problem with implanted tissue, with the hope that a remedy will be soon to follow.

Although the exact cause and mechanism of calcification is still not known with certainty, considerable progress has been made in preventing calcification of bioprosthetic implants. For example, U.S. Pat. No. 4,481,009, incorporated herein by reference, discloses a method of inhibiting the calcification of implanted tissues by incorporating a polymer into the tissue prior to implantation. This method, in one embodiment, involves contacting a fixed tissue with a first solution of a monomer which is capable of subsequent polymerization. The monomer forms covalent bonds with the reactive sites in the tissue. The tissue is then treated with a second monomer solution under polymerization conditions such that the second monomer in solution polymerizes with the first covalently-bound monomer.

While this process has been found to inhibit the formation of calcification upon implantation, the polymer is bound not only within the interstices of the tissue but also on the surface of the tissue as well. The formation of bound polymer on the surface of the tissue can be disadvantageous in some applications, as the coated tissue may be, to some degree, less biocompatable than non-coated tissue. This bioincompatability can lead to thrombus formation. The additional mass contributed by the surface-bound polymer may also reduce the flexibility and durability of the implanted tissue. Another disadvantage of this process is that the monomers in solution tend to polymerize with each other, thus decreasing the efficiency of the process.

Therefore, there exists a need for a method which provides for selective incorporation of a polymer within interstices of the tissue in the absence of substantial polymer formation in solution and on the surface of the tissue.

SUMMARY OF THE INVENTION

In accordance with the present invention a process for treating animal biological tissue involves fixing the tissue, impregnating the biological tissue with a first solution of a monomer capable of further polymerization under conditions sufficient to covalently bond said monomer to the tissue; contacting said tissue with a polymerization initiator; and contacting the tissue with a second monomer solution under polymerization conditions in the presence of a free-radical scavenger such that the second monomer polymerizes with the covalently-bound first monomer and the resulting polymer is concentrated in the interstices of the tissue.

DETAILED DESCRIPTION OF THE INVENTION

According to the present invention, various polymeric compounds are selectively incorporated into the interstices of the tissue to be implanted in the absence of substantial attachment of the polymers to the surface of the tissue. One advantage of incorporating a polymer in the interstices of the tissue is that this is where intrinsic calcification often occurs after implantation. By incorporating polymers into the interstices of the tissue, the potential for penetration of plasma proteins and cellular material of the host into the implanted tissue is reduced. This penetration is believed to contribute to degenerative changes in the tissue resulting in early prosthetic failure. In addition, it is believed that incorporation of the polymeric compounds may increase the mechanical strength and durability of the implanted tissue.

In accordance with the present invention, various biological tissues can be made resistant to calcification upon implantation in an animal. Such tissues are generally derived from a variety of sources such as, but not limited to, bovine, porcine, horse, sheep, kangaroo, rabbit, or human cadavers and include tendons, ligaments, bladders, heart valves, dura mater, fascia lata, amnion, collagen, and pericardium. Bovine pericardial tissue is especially suitable for use in the method of this invention.

After extraction from the animal source, the tissue is generally stored and fixed within a tissue-stabilizing pH range. A preferred pH range is from about 7.0 to about 7.6, preferably pH from about 7.1 to about 7.4. A particularly preferred pH is about 7.3. As used herein, the term "fixed" or "fixed tissue" refers to tissue which has been treated with a tanning solution such as 4% formaldehyde or aqueous solutions of glutaraldehyde, typically 0.1% to 5% by weight, for a period of time and under conditions conventionally used to prepare natural tissue for implantation. Tissue fixing procedures are well known and do not constitute a part of the present invention. Fixing biological tissue with such tanning agents as glutaraldehyde is known to cross-link proteins in the tissue, thus rendering the tissue substantially non-antigenic so that it may be implanted in an animal different from the donor animal.

Buffers used in accordance with the present invention are preferably stable and do not interfere with the stabilization process. Such buffers have a buffering capacity sufficient to maintain an acceptable pH, particularly during the fixation of the tissue. The choice of the appropriate buffer, and its concentration will depend upon specific tissue preparation conditions; variations of which have been introduced by several manufacturers. The buffer can be either conventional 0.01 to 0.02M phosphate-buffered saline(PBS) or phosphate-deficient solutions such as those containing less phosphate than the 0.01 to 0.02M PBS solutions, and preferably less than about 0.001 to about 0.002M phosphate. Preferred buffers in accordance with the present invention include borate, carbonate, bicarbonate, cacodylate (found to be non-toxic in animals), and other synthetic, artificial, or organic buffers such as N-2-hydroxyethylpiperazine-N'-2-ethanesulphonic acid (HEPES); morpholine propanesulphonic acid (MOPS); and 1,4-piperazinediethanesulphonic acid (PIPES). Tissue prepared in HEPES buffer advantageously results in a significant reduction of calcification after implantation, and is therefore most preferred in the present invention. Preferably, the buffered or unbuffered solutions used in accordance with the present invention should not interfere substantially with the tissue-stabilizing process afforded by the fixing agents such as glutaraldehyde. That is, they should not react with the fixing agent or prevent the fixing agent from achieving proper fixation of the tissue. Illustrative of these unsuitable buffers are those containing primary and secondary amines such as tris(-hydroxymethyl)aminomethane (Tris), which are known to react with the aldehyde groups of glutaraldehyde and thus interfere with the normal tissue stabilization process.

After the tissue has been fixed, it advantageously is contacted with coupling agents or spacers which are used to link the monomers in the first solution to the tissue. Alternatively, the monomers could be covalently bound directly to the tissue. Examples of various spacers or coupling agents which can be used include diamines which readily bond the free carboxyl residues on the protein and mucopolysaccharide components of the tissue. Preferably, the coupling of diamines is aided with an activating factor, such as a carbodiimide. Examples of this type of coupling are illustrated by Lloyd and Burns in *Journal of Polymer Science: Polymer Chemistry Edition*, Vol. 17, pp. 3459-3489 (1979), incorporated herein by reference. Preferred diamines in accordance with the present invention include those having the formula R—(NH$_2$)$_2$ wherein R is an aliphatic group having straight, branched, or cyclic chain; or an aromatic group. Preferably, the R group is such that the diamine can freely diffuse within the protein network of the tissue. Preferably, the diamine should be water-soluble. The most preferred diamine in accordance with the present invention is ethylenediamine. The carbodiimide activating factor is preferably water soluble. A suitable activating factor is 1-ethyl-3(3-dimethylaminopropyl)-carbodiimide-HCl.

The tissue is then contacted with a first solution of a monomer capable of further polymerization. The monomer is covalently bound to the free amino group of the diamine which was previously bound to the tissue as described above. One skilled in the art will recognize the wide variety of monomers that may be included in the first solution. This solution may contain one or more types of monomers, but preferably contains only one monomer species. When covalent bonding of the polymer to the biological tissue is desired, the monomers advantageously have certain structural characteristics. For example, the monomers should have reactive chemical groups that allow covalent bonding of the monomer to the tissue (through reactive groups on the tissue), either directly or through a spacer (described above). Preferably, the monomers are also capable of having a free radical generated at a position that allows subsequent reaction with the monomers in the second solution, such that the tissue-bound polymer is formed in situ. In one embodiment of the invention, the first monomer solution contains a monomer chosen from acrylic acid, methacrylic acid or derivatives thereof including amides and esters thereof. Preferably, the first solution contains acrylic acid. By contacting the tissue with a first monomer solution, the monomers can either be impregnated into the biological tissue by inclusion within the interstices of the tissue to form a physical or mechanical bond, or they can be covalently bonded thereto. Preferably, the monomer becomes covalently bound to the tissue, as it is less likely to dislocate within the layers of the tissue after implantation. A number of functional chemical groups in the protein structure of the tissue provide sites for covalent bonding with the monomers. Examples of such functional groups include α- and ε-amino groups; α-, β-, and γ-carboxyl groups; the sulfhydryl and hydroxyl groups of cysteine and serine; the imidazole group of histidine; and the phenol ring of tyrosine. In addition, the mucopolysaccharides of the biological tissue have free carboxyl groups on which a variety of monomers can be attached. When the tissue has been tanned with agents such as glutaraldehyde, the "fixing" process will have substantially cross-linked the free amino groups of the tissue so that they generally are not available for bonding.

After the fixed tissue has been impregnated with the first monomer solution, the tissue is advantageously rinsed in order to remove any non-covalently bonded monomer entrapped within the tissue. This non-covalently bonded monomer would compete (during subsequent steps) with those monomers which are bound to the tissue and thus decrease the efficiency and selectivity of polymerization in the method of the present invention.

After the non-covalently bonded monomers are removed, the tissue is contacted with or exposed to a polymerization or free-radical initiator. Many types of such initiators are known in the art, including ionizing radiation, ultraviolet radiation, thermal radical initiators, redox polymerization initiators, chemicals such as certain peroxides or persulfates, etc. Any suitable conventional initiator can be used, including aqueous solutions of ammonium persulfate containing minor amounts of N,N,N',N'-tetramethylenediamine. The polymerization initiator is employed in an amount which catalyzes the reaction of the covalently-bound monomer with monomers added subsequently and initiates polymerization of said subsequently added monomers.

Once the free radicals of the bound monomers have been generated, the tissue is contacted with a second monomer solution. The monomers that are present in this second solution can be the same or different from those used in the first solution.

One skilled in the art will recognize the wide variety of suitable monomers that may be included in this second solution. The monomers should be chosen so that the tissue having the resulting polymer incorporated therein will have the properties required for its intended use. For example, tissue which will be subjected to stretching or flexing after implantation desirably has an elastomeric polymer incorporated therein, as described in copending U.S. patent application Ser. No. 795,125, filed of even date herewith. Durability is another desirable property so that the polymer will remain intact within the implanted tissue for extended periods of time. The polymer should also be sufficiently biocompatible to be suitable for implantation adjacent to living tissues. The monomers in the second solution preferably have reactive double bonds (e.g., are ethylenically unsaturated) to promote polymerization.

If desired, a mixture of oligomers can be employed in the second monomer or oligomer solution to produce a block copolymer. If a mixture of oligomers is employed, the oligomers are generally short enough in chain length that they can diffuse freely through the interstices of the biological material. The chain length generally ranges from about 5 to 50 monomers, preferably about 10 to 20. Such oligomers are preferably vinyl-terminated so that they can further polymerize after being contacted with the first monomer.

The second monomer solution may contain one or more monomers and/or oligomers. In one embodiment of the invention, the solution contains monomers chosen from acrylic acid, methacrylic acid and derivatives thereof including amides and esters thereof. The monomers are suspended in the second monomer solution in amounts of from about 0.1 to about 10 weight percent, preferably about 0.5 to about 6 weight percent of the total weight of the solution. Most preferably, the monomers comprise to about 0.5 to about 2 weight percent of the solution.

In addition to the monomers that are present in the second solution, conventional cross-linkers are generally present in conventional amounts. One example of a cross-linking agent which has been found particularly useful in the present invention is bisacrylamide. The degree of cross-linking in the polymers can be controlled by the amount of cross-linker that is present. Generally, the cross-linking agent is present in amounts of from about 0.02 to about 1.0, preferably from about 0.1 to about 0.4 weight percent of the solution, with about 0.25 weight percent being most preferred.

To get the desired selective incorporation, a free-radical quencher or scavenger is present in the second monomer solution. Free-radical scavengers are commonly used in certain polymerization procedures to reduce homopolymerization, i.e., polymerization of monomers in solution. Homopolymerization may reduce the efficiency of a desired polymerization reaction, since a percentage of monomers in the second monomer solution are polymerizing with each other in solution rather than polymerizing with the monomers from the first solution. Working with tissue in a solution in which substantial homopolymerization has taken place can also pose difficulties, since it is immersed in a gelatinous, viscous, and/or sticky polymer that may be difficult to remove prior to implantation.

When a free-radical scavenger was included in the second monomer solution in the method of the present invention, it was found that homopolymerization was inhibited and, unexpectedly, that the polymer covalently bound to the tissue was substantially confined to the interstices of the tissue. While the invention is not limited to any particular theory, it appears that a free-radical quencher used in the process of the present invention selectively quenches free radicals in the second monomer solution and on the tissue surface, while leaving a high percentage of free radicals in the interior portions of the tissue unaffected. This selective incorporation of polymer into the interstices of the tissue is advantageous, because problems associated with polymer-coated tissue surfaces in some applications are avoided. Such problems include reduced biocompatibility (when compared with the natural tissue surface) which may cause thrombus formation, and reduced flexibility and/or durabiity of the tissue due to the additional mass contributed by the surface-bound polymer. Another advantage is the selective incorporation of the polymer at the site at which intrinsic calcification often occurs after implantation, namely, the interstices of the tissue.

Any of the free-radical scavengers known in the art which reduce homopolymerization without retarding the desired polymerization process may be used. Examples of free-radical scavengers that can be used in the present invention include ferrous ammonium sulfate, ascorbic acid, potassium ferricyanide, and cupric ion (e.g., cupric nitrate), with ferrous ammonium sulfate, which is suitably biocompatible and does not cause discloration of the polymer, being preferred.

There is competition between polymerization involving the generated free radicals, and quenching of those free radicals by the ferrous ammonium sulfate. By varying the amount of free-radical scavenger that is present in the second monomer solution, the degree of polymerization occurring in the solution (i.e., homopolymerization) and on the tissue surface can be controlled. The free-radical scavenger advantageously is present in amounts which allow the polymerization of the covalently-bound monomers in the intersteces of the tissue and substantially quench free radicals on the covalently-bound monomers on the surface of the tissue as well as the monomers in the solution. Generally, the concentration of the free-radical scavenger can range from about 0.1 to about 0.4 weight percent of the second monomer solution, preferably from about 0.2 to about 0.3 weight percent, and most preferably 0.25 weight percent.

While the tissue is being contacted with the second monomer solution, polymerization of the monomers occurs. It is preferred that the polymerization reaction be carried out in an inert atmosphere with a nitrogen atmosphere being particularly preferred, and that solutions which contact the tissue during and after the free-radical initiation step are advantageously purged with nitrogen prior to use. The reaction is carried out for a time sufficient to provide for substantial polymerization of the covalently bound monomer with the monomers in solution.

After the polymerization reaction is completed, the tissue is rinsed and sterilized. The tissue can be sterilized by any conventional means, including exposure to ethylene oxide or immersion in a solution containing glutaraldehyde or about 4–5% formaldehyde. A sterilizing solution containing 4–5% formaldehyde may contain additional substances such as ethanol, surfactants, and buffering compounds. Thereafter, the tissue is rinsed and is ready for implantation.

Biological tissues treated by the method of this invention have been shown, by differential staining procedures, to have the polymeric material concentrated in the interior portions of the tissue. The outer surface regions are substantially devoid of polymer and thus present a more natural surface after implantation for contact with blood and other living tissues.

The present invention is further illustrated by the following examples which are not intended to be limiting. The present invention has been described in specific detail and in reference to its specific embodiments; however, it is to be understood by those skilled in the art that modifications and changes can be made thereto without departing from the spirit and scope thereof.

EXAMPLE I

Extracted bovine pericardial tissue was thoroughly rinsed and shipped in an isotonic (285±15 milliosmols) solution containing 0.54 grams/liter of the sodium salt of HEPES and 0.885 weight percent sodium chloride at pH 7.3 at about 4° C.; and fixed with 0.625 weight percent glutaraldehyde in an isotonic solution containing 5.39 grams/liter of the sodium salt of HEPES, 0.440 weight percent sodium chloride, and 2.6 grams/liter of $MgCl_2.6H_2O$ at room temperature.

A portion of the extracted and fixed tissue was further sterilized in a solution containing about 4 percent formaldehyde. The sterilizing solution comprised either 4% formaldehyde alone or a 4% formaldehyde/22.5% ethanol/1.2% Tween - 80 TM solution buffered with HEPES, pH 7.4. The tissue was then rinsed in sterile saline to remove residual glutaraldehyde at a time immediately prior to implantation, and implanted subcutaneously in growing rabbits. The tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections. This implanted tissue did not have a polymer incorporated therein and thus served as a control.

Another portion (about 5 grams wet weight) of the extracted and fixed tissue was immersed in a 40 ml solution containing about 2.5 grams of ethylenediamine at pH 4.75. After about 30 minutes, 2 grams of water-soluble 1-ethyl-3(3-dimethylaminopropyl) carbodiimide-HCl were added stepwise while the pH was maintained at 4.75 for a 30 minute incubation period at room temperature. The pH is preferably controlled to 4.75±0.1 in order to ensure maximum reactivity of the diamine with the carboxylate groups on the tissue. Next, the tissue was rinsed thoroughly with HEPES-buffered-saline at pH 7.4 and transferred into an aqueous solution containing 0.2M acrylic acid at pH 4.75 for about 30 minutes. The tissue was then thoroughly rinsed with HEPES-buffered-saline to remove any non-coupled acrylic acid from the tissue. The acrylic acid-coupled tissue was then further suspended in about 40 ml distilled water and bubbled with nitrogen for about 30 minutes before replacing with a 40 ml solution of 2 percent ammonium persulfate containing 0.6 percent (v/v) N,N,N',N'-tetramethylenediamine which had been previously bubbled with nitrogen for 30 minutes. After 30 minutes, the free radical initiation step was completed, and the tissue was transferred to 40 ml of a 1 weight percent acrylamide solution containing 0.25 percent bisacrylamide (N,N'-methylbisacrylamide) and 0.25 weight percent ferrous ammonium sulfate. All tissue transfer steps were performed in a nitrogen atmosphere. After the reaction mixture was allowed to polymerize for about 60 minutes, the tissue was rinsed with distilled water and then sterilized in a solution containing 4 percent formaldehyde. The sterilizing solution comprised either 4% formaldehyde alone or a 4% formaldehyde/22.5% ethanol/1.2% Tween - 80 TM solution buffered with HEPES, pH 7.4. The tissue was then rinsed again in sterile saline and implanted subcutaneously in growing rabbits. The tissue was retrieved up to six weeks later at regular one-week intervals; and the extent of tissue calcification was assessed by quantitatively monitoring the weight percent calcium in dried tissue using atomic absorption analysis, and histologically by visually monitoring the degree of calcification in Von Kossa-stained tissue sections. Both the histologic and quantitative results indicate that the implanted tissue having acrylamide incorporated therein effected a significant reduction in calcification compared to the control tissue. The results are in Table 1, which show a quantitative evaluation of the degree of calcification on a scale of 0, 1, 2, and 3 using Von Kossa stain, where "3" represents significant calcification, with higher values being possible.

A portion of the tissue prepared above with the polymer incorporated therein was stained with coomassie blue, which is a commonly-used protein-specific dye. The dye which was not bound to protein was washed away by "destaining" in 7 percent acetic acid. Areas of the tissue having polymer bound thereto will not be stained because the polymer prevents binding of the dye to the proteins in the biological tissue. Examination of a cross-section of the tissue showed blue stain on the outer surfaces of the tissue, while the middle, "internal" portion of the tissue was unstained. Thus, the polymer was found to be selectively incorporated into the interstices of the tissue. In addition, virtually no homopolymerization occured when the tissue was immersed in the second monomer solution, which contained the free-radical scavenger.

Biological tissue prepared according to the process of the invention was therefore shown to mitigate calcification after implantation and to have the desired selective incorporation of the polymer in the interstices of the tissue while the surface remained substantially polymer-free. The advantages of implantable tissues having these properties were discussed above.

TABLE 1

Effect of Polymer-Incorporating Treatment of Pericardial Tissue on the Degree of Calcification in Growing Rabbits

| Implant Time (in weeks) | Treatment | |
| --- | --- | --- |
|  | Polymer | Control |
| 1 | 0.0 ± 0.0 | 0.0 ± 0.0 |
|  | n = 2 | n = 2 |
| 2 | 0.0 ± 0.0 | 1.0 ± 0.5 |
|  | n = 2 | n = 2 |
| 3 | 0.0 ± 0.0 | 1.8 ± 1.3 |
|  | n = 2 | n = 2 |
| 4 | 0.0 ± 0.0 | 2.8 ± 0.3 |
|  | n = 2 | n = 2 |
| 5 | 0.0 ± 0.0 | 2.8 ± 0.3 |
|  | n = 2 | n = 2 |

TABLE 1-continued
Effect of Polymer-Incorporating Treatment of Pericardial Tissue on the Degree of Calcification in Growing Rabbits

| Implant Time (in weeks) | Treatment Polymer | Control |
|---|---|---|
| 6 | 0.0 ± 0.0<br>n = 2 | 3.0 ± 0.0<br>n = 2 |

I claim:

1. A process for treating animal biological tissue prior to implantation in an animal to reduce calcification of said tissue after implantation comprising the steps of:
   (a) fixing said tissue under tissue-fixing conditions;
   (b) contacting said fixed tissue with a first solution of one or more monomers under conditions sufficient to covalently bond said monomer(s) to the tissue;
   (c) contacting said tissue with a polymerization initiator; and
   (d) contacting said tissue with a second solution containing one or more monomers or oligomers under polymerization conditions in presence of a polymerization-inhibiting free-radical scavenger, such that the second monomer(s) or oligomer(s) polymerize with said covalentyl-bound first monomer(s) and the resulting polymer is concentrated in the interstices of the tissue.

2. The process of claim 1 wherein said free-radical scavenger is selected from the group consisting of ferrous ammonium sulfate, ascorbic acid, potassium ferricyanide, or cupric nitrate.

3. The process of claim 1 wherein said free-radical scavenger is ferrous ammonium sulfate and said polymerization initiator is an aqueous solution containing ammonium persulfate and N,N,N',N'-tetramethylenediamine.

4. The process of claim 1 wherein said free-radical scavenger is present in the second monomer solution in an amount effective in minimizing homopolymerization of the second monomers in solution and selectively quenching free radicals on the outer surfaces of the tissue, without substantially quenching free radicals in the interior portions of the tissue.

5. The process of claim 4 wherein said free-radical scavenger is present in the second monomer solution in amounts of from about 0.15 to about 0.4 weight percent of the total weight of said solution.

6. The process of claim 5 wherein said free-radical scavenger is present in the second monomer solution in amounts of from about 0.2 to about 0.3 weight percent of the total weight of said solution.

7. The process of claim 6 wherein said second monomer solution contains about 0.25 weight percent of said free-radical scavenger.

8. The process of claim 1 further comprising the step of removing the non-covalently bound monomer from said tissue between steps (b) and (c).

9. The process of claim 1 wherein said first monomer solution contains acrylic acid, methacrylic acid and/or derivatives thereof, including amides and esters thereof.

10. The process of claim 1 wherein said second monomer solution comprises acrylamide, acrylic acid, esters of acrylic acid, methacrylic acid, methacrylamide, esters of methacrylic acid or mixtures thereof.

11. The process of claim 1 wherein said first monomer is acrylic acid or methacrylic acid, and said second monomer solution comprises acrylamide, acrylic acid, esters of acrylic acid, methacrylic acid, methacrylamide, esters of methacrylic acid or mixtures thereof.

12. The process of claim 1 wherein the first monomer covalently bound to said tissue is acrylic acid, and the second monomer is acrylamide.

13. The process of claim 1 wherein said second solution additionally comprises a cross-linking agent.

14. The process of claim 13 wherein said cross-linking agent is bisacrylamide.

15. The process of claim 14 wherein said second solution contains about 0.25 weight percent of bisacrylamide.

16. The process of claim 1 wherein monomers are suspended in the second monomer solution in amounts of from about 0.1 to about 10.0 weight percent of the total weight of the solution.

17. The process of claim 16 wherein monomers are suspended in the second monomer solution in amounts of from about 0.5 to about 6.0 weight percent of the total weight of the solution.

18. The process of claim 17 wherein monomers are suspended in the second monomer solution in amounts of from about 0.5 to about 2.0 weight percent of the total weight of the solution.

19. The process of claim 1, wherein said biological tissue is a tendon, ligament, heart valve, dura mater, fascia lata, amnion, or pericardium taken from a bovine, porcine, horse, sheep, kangaroo, rabbit, or human cadaver source.

20. The process of claim 1 wherein said biological tissue is fixed with glutaraldehyde.

21. The process of claim 1 further comprising covalently binding a spacer to said fixed tissue between steps (a) and (b) so that the monomer(s) in said first solution is/are covalently bound to said tissue through the spacer.

22. The process of claim 21 wherein said spacer is a diamine compound.

23. The process of claim 22 wherein said diamine compound has the formula $R—(NH_2)_2$, wherein R is an aliphatic group having a straight, branched or cyclic chain, or an aromatic group.

24. The process of claim 23 wherein said diamine compound is ethylenediamine.

25. The process of claim 22 wherein said diamine is covalently bound to said fixed tissue in the presence of a carbodiimide.

26. A process for treating animal biological tissue prior to implantation in an animal to reduce calcification of said tissue after implantation comprising steps of
   (a) fixing said tissue under tissue-fixing conditions;
   (b) contacting said tissue with a first solution containing one or more monomers capable of further polymerization under conditions sufficient to impregnate said monomer(s) in said tissue; and
   (c) contacting said tissue with a second solution containing one or more monomers or oligomers under polymerization conditions in the presence of a polymerization-inhibiting free-radical scavenger, such that the second monomer(s) or oligomer(s) polymerize with said first monomer(s) and the resulting polymer is concentrated in the interstices of the tissue.

27. The process of claim 26 wherein said first monomer solution comprises acrylic acid, methacrylic acid, and/or derivatives thereof, including amide and ester derivatives thereof.

28. The process of claim 26 wherein said second monomer solution comprises acrylamide, acrylic acid, esters of acrylic acid, methacrylic acid, methacrylamide, esters of methacrylic acid or mixtures thereof.

29. Biological tissue having a reduced tendency toward calcification after implantation in an animal, said tissue having a polymer incorporated therein according to the process of claim 1, 21, or 26.

* * * * *